(12) United States Patent
Liu

(10) Patent No.: US 6,175,023 B1
(45) Date of Patent: Jan. 16, 2001

(54) SYNTHESIS OF WATER SOLUBLE 9-DIHYDRO-PACLITAXEL DERIVATIVES FROM 9-DIHYDRO-13-ACETYLBACCATIN III

(75) Inventor: Jian Liu, 470 Cherry Ave., Fredericton, New Brunswick (CA), E3A 5N9

(73) Assignee: Jian Liu, Fredericton (CA)

( * ) Notice: Under 35 U.S.C. 154(b), the term of this patent shall be extended for 0 days.

(21) Appl. No.: 09/494,629

(22) Filed: Jan. 31, 2000

(51) Int. Cl.[7] .................................................. C07D 305/14
(52) U.S. Cl. ........................................... 549/510; 549/511
(58) Field of Search ...................... 549/510, 511

(56) References Cited

U.S. PATENT DOCUMENTS 5,352,806    10/1994    Gunawardana et al. ............. 549/510

FOREIGN PATENT DOCUMENTS

WO 93/21173    10/1993    (WO) ........................... C07D/305/14

98/50378 * 11/1998 (WO) ................................... 549/510

* cited by examiner

*Primary Examiner*—Charanjit S. Aulakh
(74) *Attorney, Agent, or Firm*—Paul S. Sharpe; Marks & Clerk

(57) ABSTRACT

Compounds of the formula of

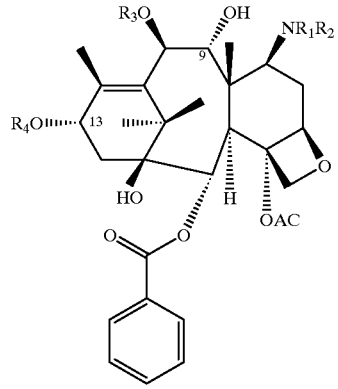

are disclosed as well as a method of preparation.

4 Claims, No Drawings

SYNTHESIS OF WATER SOLUBLE 9-DIHYDRO-PACLITAXEL DERIVATIVES FROM 9-DIHYDRO-13-ACETYLBACCATIN III

FIELD OF THE INVENTION

The present invention relates to the semisynthesis of paclitaxel derivatives, and more particularly, the present invention relates to the semisynthesis of 9-dihydrotaxanes using 9-dihydro-13-acetylbaccatin III as the initial compound.

BACKGROUND OF THE INVENTION

Paclitaxel (taxol) is a well known chemotherapeutic agent having efficacy against a broad range of cancers. It has been shown to be clinically effective against ovarian and breast cancer, and has exhibited promising activity against a number of other types of cancers such as liver, peritoneal, cervical, prostate, colon and esophageal.

Conventionally, taxol is obtained by extraction from the bark of the Pacific *Taxus brevifolia*. However, the isolation of taxol from the tree bark is a difficult, low-yield and expensive process. Further, the scarcity of the yew has prompted, scientists to explore alternate routes.

Although paclitaxel is a promising drug for the treatment of ovarian and breast cancers, the low water solubility of paclitaxel can be problematic. In a quest for new derivatives with potentially enhanced solubility, one of the sites on the molecule where attention has been directed is the ketone function at the C-9 position, or conversion at the C-10 acetate group on the taxane nucleus to a hydroxyl group.

Previous attempts to improve water solubility have also relied on the preparation of water soluble pro-drugs, which are converted to paclitaxel under physiological conditions, or novel drug formulations.

An alternative method of increasing water solubility of palitaxel would be to replace one of the hydroxyl groups with an amino group; salts of the resulting amine would have improved water solubility.

In the search for alternative solutions, the discovery of new taxol derivatives having broader spectrum, enhanced in vivo activity and improved water solubility and stability have been reported. Among the compounds reported, those belonging to the 9-dihydrotaxane family show great promise. Thus far, only limited members of that family, including 9-dihydrotaxol and 9-dihydrotaxotere, have been successfully synthesized. The ability to synthesize a greater number of 9-dihydrotaxane compounds having superior pharmacologic properties would be a valuable asset.

SUMMARY OF THE INVENTION

In accordance with one aspect of one embodiment of the present invention, there is provided an improved method of synthesizing 9-dihydrotaxane compounds.

In accordance with a further aspect of one embodiment of the present invention, there is provided a compound having the formula:

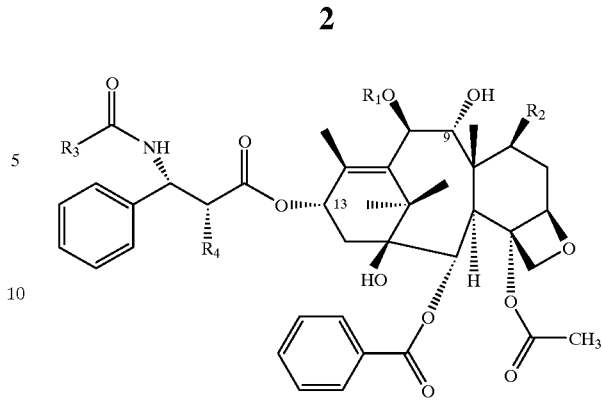

wherein $R_1$ is Ac or H; $R_2$ is O—Si $(C_2H_5)_3$, $NH_2$, O-Tosyl, or NH∿∿∿$NH_2$; $R_3$ is $C_5H_{11}$ or Phenyl; and $R_4$ is OH or $NH_2$.

In a further aspect of one embodiment of the present invention, there is provided a compound having the formula:

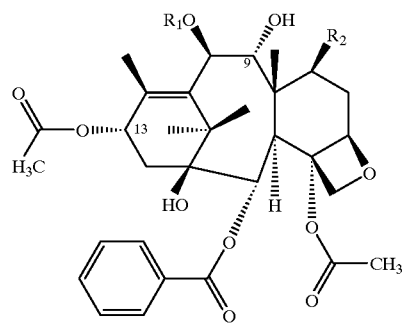

wherein $R_1$ is Ac or H and $R_2$ is O—Si$(C_2H_5)$3, $NH_2$, O-Tosyl, or $NHCH_2$ $CH_2NH_2$ In a still further aspect of one embodiment of the present invention, there is provided a compound having the formula:

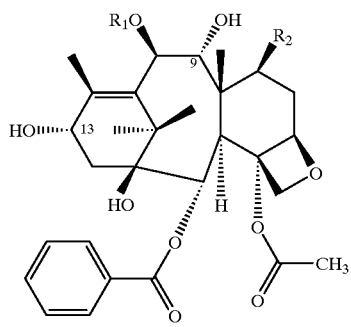

wherein $R_1$ is H and $R_2$ is O—Si$(C_2H_5)_3$, O—Tosyl, $NH_2$ or NH∿∿∿$NH_2$ Regarding a further aspect of one embodiment of the present invention, there is provided a process for preparing 9-dihydrotaxane, comprising the steps of:
(a) protecting the C-7 hydroxy group of 9-dihydro-13-acetylbaccatin III with a suitable protecting group;
(b) deacetylating the product of step (a) at the C-13 position; and
(c) adding a suitable side chain to the C-13 position of the product obtained in step (b).

DETAILED DESCRIPTION OF THE PREFERRED EMBODIMENTS

Taxane derivatives synthesized in accordance with the present invention are characterized by the following chemical structure:

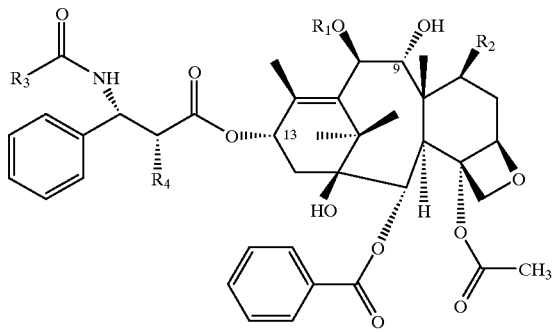

7-amino-9-dihydrotaxol C, wherein
$R_1$ is Ac
$R_2$ is $NH_2$
$R_3$ is $C_5H_{11}$
$R_4$ is OH
7-amino-10-deacetyl-9-dihydrotaxol C, wherein
$R_1$ is H
$R_2$ is $NH_2$
$R_3$ is $C_5H_{11}$
$R_4$ is OH
2'-amino-9-dihydrotaxol, wherein
$R_1$ is AC
$R_2$ is OH
$R_3$ is $C_6H_5$
$R_4$ is $NH_2$
2'-amino-10-deacetyl-9-dihydrotaxol, wherein
$R_1$ is H
$R_2$ is OH
$R_3$ is $C_6H_5$
$R_4$ is $NH_2$
7-amino-9-dihydrotaxol, wherein
$R_1$ is Ac
$R_2$ is $NH_2$
$R_3$ is $C_6H_5$
$R_4$ is OH
7-amino-10-deacetyl-9-dihydrotaxol, wherein
$R_1$ is H $R_2$ is $NH_2$ $R_3$ is $C_6H_5$
$R_4$ is OH
7-aminoethylamino-9-dihydrotaxol, wherein
$R_1$ is Ac
$R_2$ is NH $NH_2$
$R_3$ is $C_6H_5$
$R_4$ is OH 9-dihydro-13-acetylbaccatin IIII is used as the starting material in the preparation of the above 9-dihydrotaxanes. 9-dihydro-13-acetylbaccatin III can be extracted from the Taxus species, preferably *Taxus canadensis*.

In overview, plant material such as stems and needles are collected, ground and extracted with methanol. The extraction continues for 24 hours at room temperature, and is filtered. The extract is concentrated to about 10% of its original volume by evaporation, and an equal amount of water is added to the concentrate. The aqueous solution is extracted several times with hexane to give an aqueous layer and a non-aqueous layer. The aqueous layer is extracted several times with chloroform or dichloromethane. The chloroform or dichloromethane extract is concentrated to dryness, and the residue is dissolved in a mixture of chloroform, methanol and acetone in a ratio of approximately 10:1:0.5 and fractionated by dry column chromatography to obtain several fractions containing taxol and 9-dihydro-13-acetylbaccatin III. The fractions are combined and extracted with methanol. The methanol extract is concentrated to dryness, and the residue is dissolved in methanol to crystallize out the 9-dihydro-13-acetylbaccatin III.

The processes of the present invention, as illustrated below in Schemes 1 to 4(b), include the steps of:

(a) protecting the C-7 hydroxy group of 9-dihydro-13-acetylbaccatin III with a suitable protecting group;

(b) deacetylating the product of step (a) at the C-13 position; and (c) adding a suitable side chain to the C-13 position or the product obtained in step (b).

The processes may further include the step of removing the protecting group of the product obtained in step (c).

Referring to Scheme 1,7-amino-9-dihydrotaxol C may be obtained by adding a protecting group, for example a Tosyl group such as tosyl chloride to 9-dihydro-13-acetylbaccatin IIII at the C-7 position in the presence of a suitable catalyst, preferably a substituted amine such as tetrabutylammonium iodide, and a non-polar solvent such as dichloromethane. Compared to the prior art method, it was found that the tetrabutylammonium iodide/dichloromethane combination improves the yield of the desired product. Other advantages such as a short reaction time, an easy purification of the product and a relatively small amount of byproducts being produced were also noted. Advantageously, the above reagents are less toxic which can be beneficial in large scale production. The mixture is stirred at room temperature until the reaction is completed, following which it is extracted with a non-polar solvent such as dichloromethane. The organic phase is concentrated to dryness under vacuum and purified by a chromatography method, preferably normal flash column chromatography, eluting with suitable solvent systems such as dichloromethane and methanol in a ratio of 97:3 to yield the intermediate 7-O-tosyl-9-dihydro-13-acetylbaccatin III.

The 7-O-tosyl-9-dihydro-13-acetylbaccatin III intermediate is deacetylated at the C-13 position by reaction with an alkyl lithium, for example methyl lithium, or using Red-Al. The resulting mixture is partitioned between a solvent system consisting of a buffer such as sodium hydrogencarbonate of ammonium chloride and a non-polar solvent such as dichloromethane. The organic layer is concentrated to dryness, and the crude product is purified by, for example flash column chromatography, using a solvent system such as dichloromethane and methanol in a ratio of 97:3 to yield the intermediate 7-O-tosyl-9-dihydrobaccatin III.

The 7-O-tosyl-9-dihydrobaccatin III intermediate is further treated with 2'-ethoxyethyl-N-hexanoyl-(2R,3S)-3-phenyl-isocrine in the presence of a strong nucleophilic reagent, for example, an alkylsilyl lithium such as lithium hexamethyldisilazide. The mixture is quenched with a suitable solvent such as a mixture of a buffer such as pH 7 phosphate and non-polar solvent such as dichloromethane, or THF. The organic phase is concentrated to dryness and the residue purified by, for example, flash column chromatography, eluting with a solvent mixture such as ethyl acetate and hexane (6:4) to give the 2'-ethoxyethyl-7-O-tosyl-9-dihydrotaxol C intermediate. The intermediate was treated with sodium azide, and then with Pd/C to yield an intermediate 2'-ethoxyethyl-7-amino-9-dihydrotaxol C.

The 2'-ethoxyethyl-7-amino-9-dihydrobaccatin C intermediate is further treated with 1% hydrochloric acid at 0° C. in an alcohol such as ethanol to yield the product 7-amino-9-dihydrotaxol C.

Similarly, as shown in Scheme 2(a), 7-amino-10-deacetyl-9-dihydrotaxol C may be obtained by using a nucleophilic reagent such as sodium methoxide instead of sodium hydride to yield the 13-acetyl-10-deacetyl-9-dihydro-7-O-tosyllbaccatin III intermediate. The sodium methoxide/dichloromethane combination was also found to provide superior results as in the case of the triethylamine/dichloromethane combination.

Referring to Scheme 2(b), 7-amino-10-deacetyl-9-dihydrotaxol C may also be obtained by adding a nucleophilic reagent such as sodium methoxide and 1% hydrochloric acid to the intermediate 2'-ethoxyethyl-7-amino-9-dihydrotaxol C intermediate obtained in Scheme 1.

Referring to Scheme 3, 2'-amino-9-dihydrotaxol may be obtained by adding a protecting group, preferably a silyl protecting group such as triethylsilyl to the C-7 position of 9-dihydro-13-acetylbaccatin III in the presence of a solvent mixture such as $Et_3N$ and a nucleophilic reagent such as sodium hydride in $CH_2Cl_2$. The mixture is quenched in a mixture of buffer such as pH 7 phosphate and a non-polar solvent such as dichloromethane. The organic layer is concentrated to dryness under vacuum, and the residue purified by chromatographic method, preferably is flash column chromatography. A suitable eluting solvent system, for example dichloromethane and methanol (96:4) is used to yield the intermediate 13-acetyl-9-dihydro-7-triethylsilylbaccatin III.

In a similar manner as shown in Scheme 4, 2'-amino-10-deacetyl-9-dihydrotaxol may be obtained. In this case, sodium methoxide is used instead of sodium hydride.

It was found that the presence of the triethylsilyl protecting group renders the dihydrotaxol analogues more stable.

Having thus described the invention, reference will now be made to the examples.

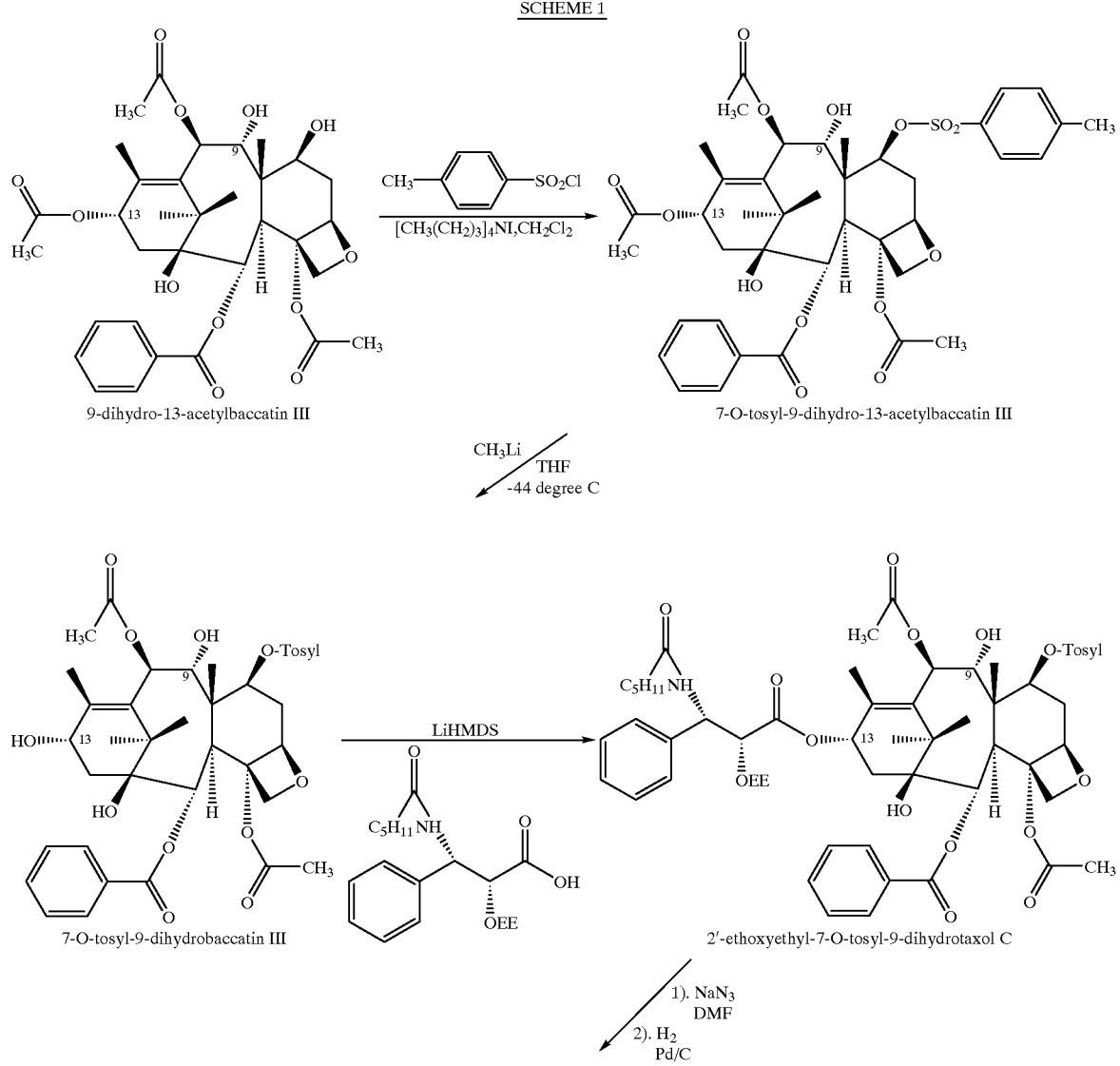

SCHEME 1

-continued
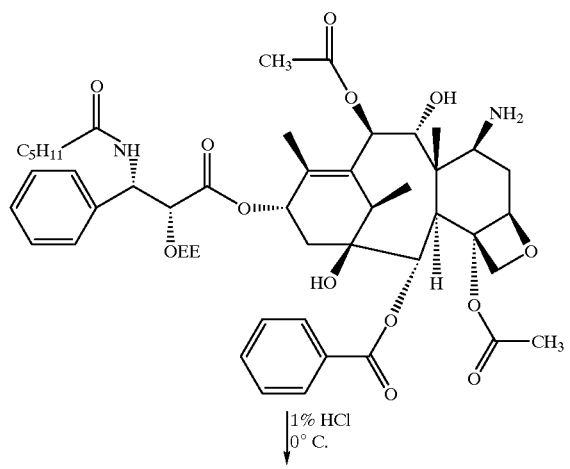
↓ 1% HCl
0° C.
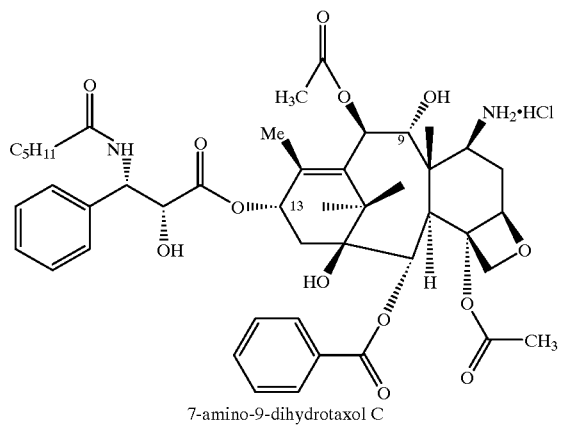
7-amino-9-dihydrotaxol C
SCHEME 2(a)
Method 1
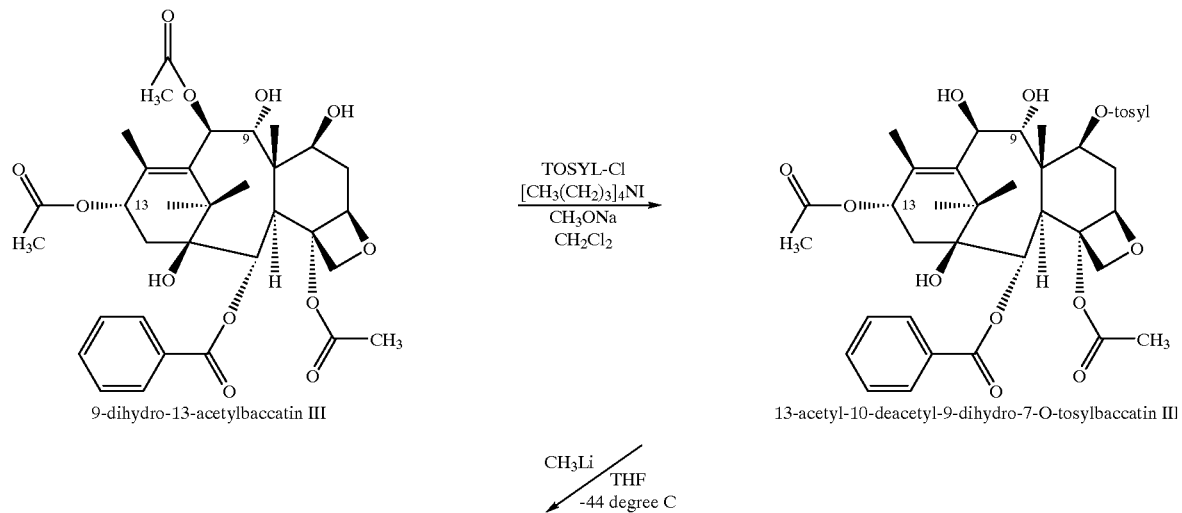

-continued
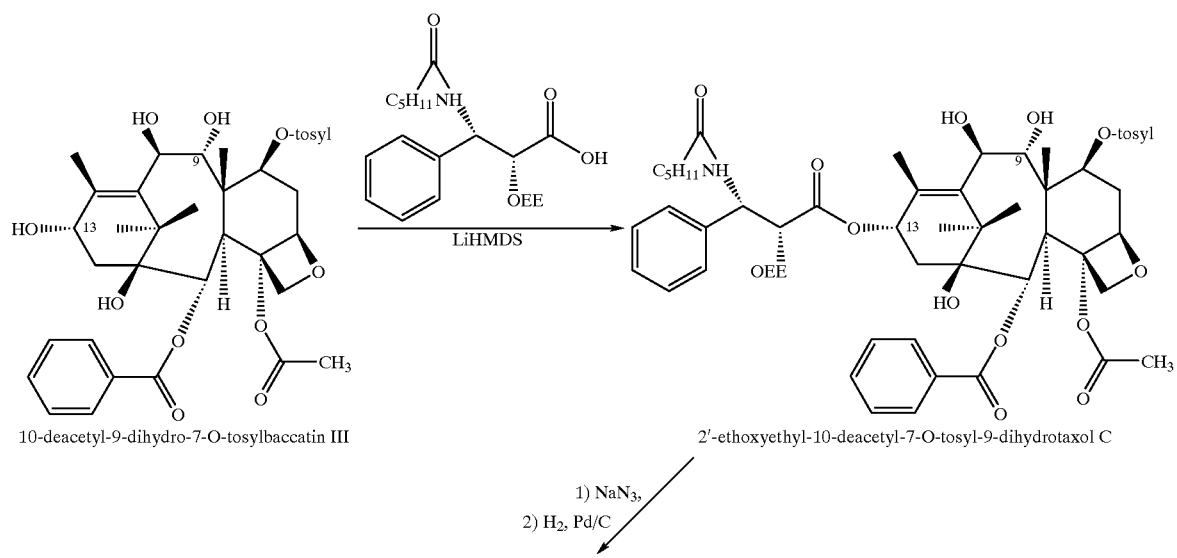
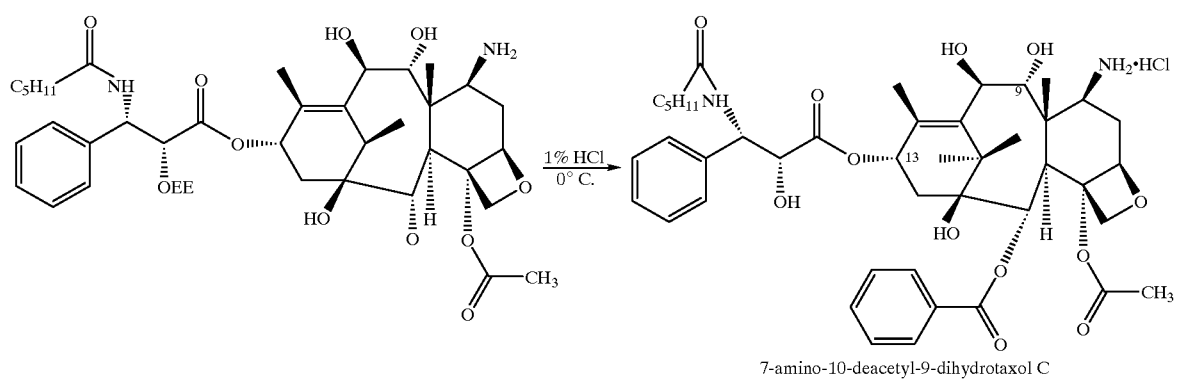
SCHEME 2(b)
Method 2
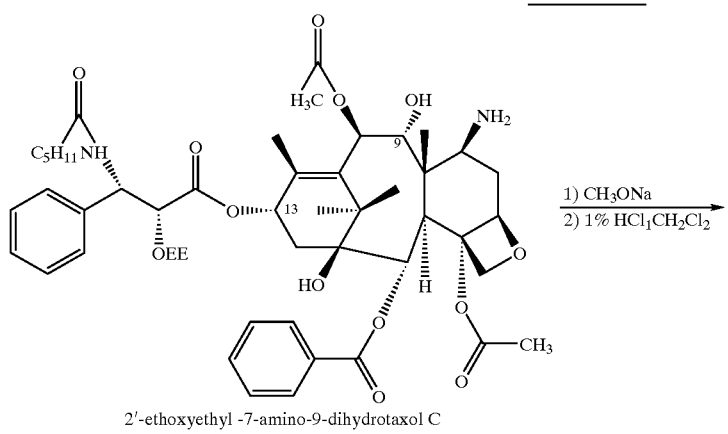

-continued
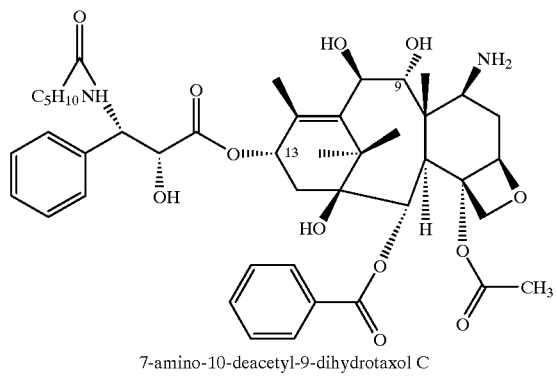
7-amino-10-deacetyl-9-dihydrotaxol C
SCHEME 2(c)
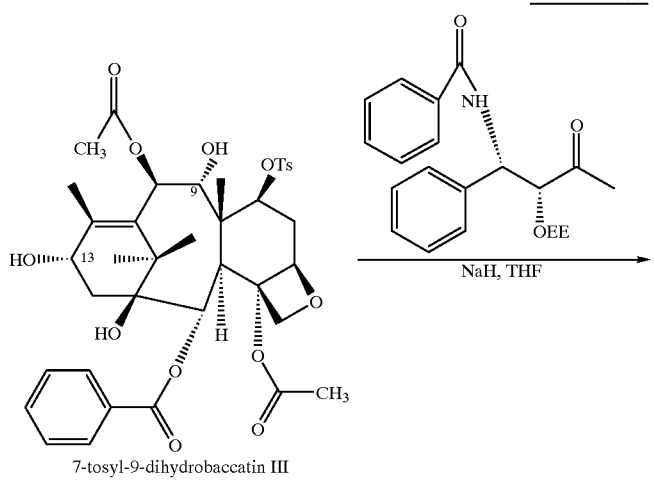
7-tosyl-9-dihydrobaccatin III
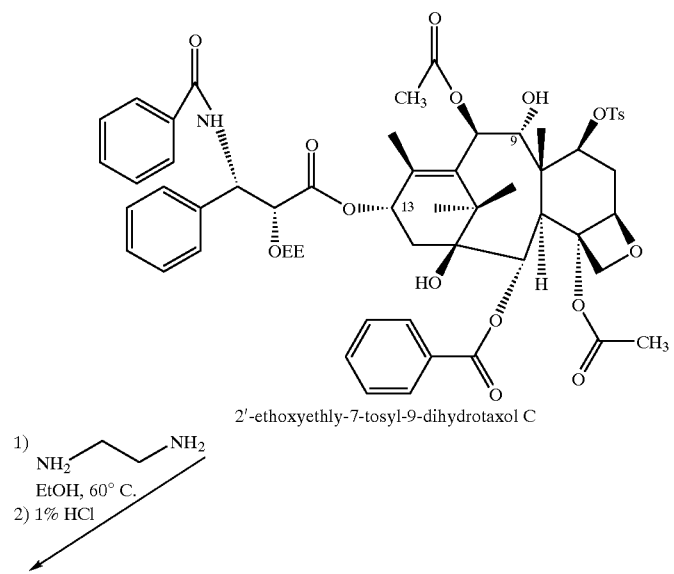
2'-ethoxyethly-7-tosyl-9-dihydrotaxol C
1) H₂N-CH₂CH₂-NH₂
   EtOH, 60° C.
2) 1% HCl

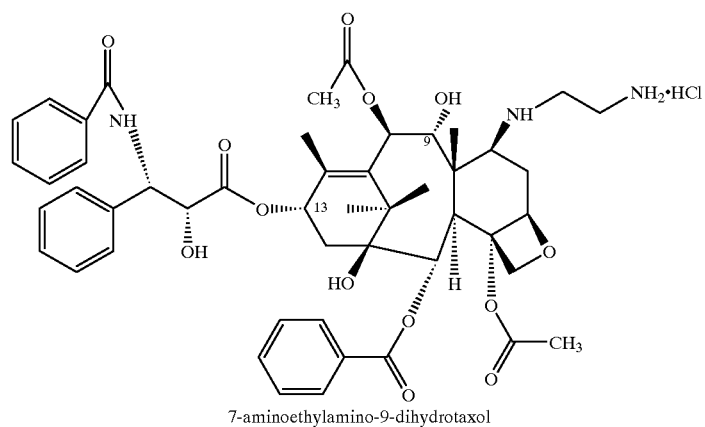
7-aminoethylamino-9-dihydrotaxol
SCHEME 3
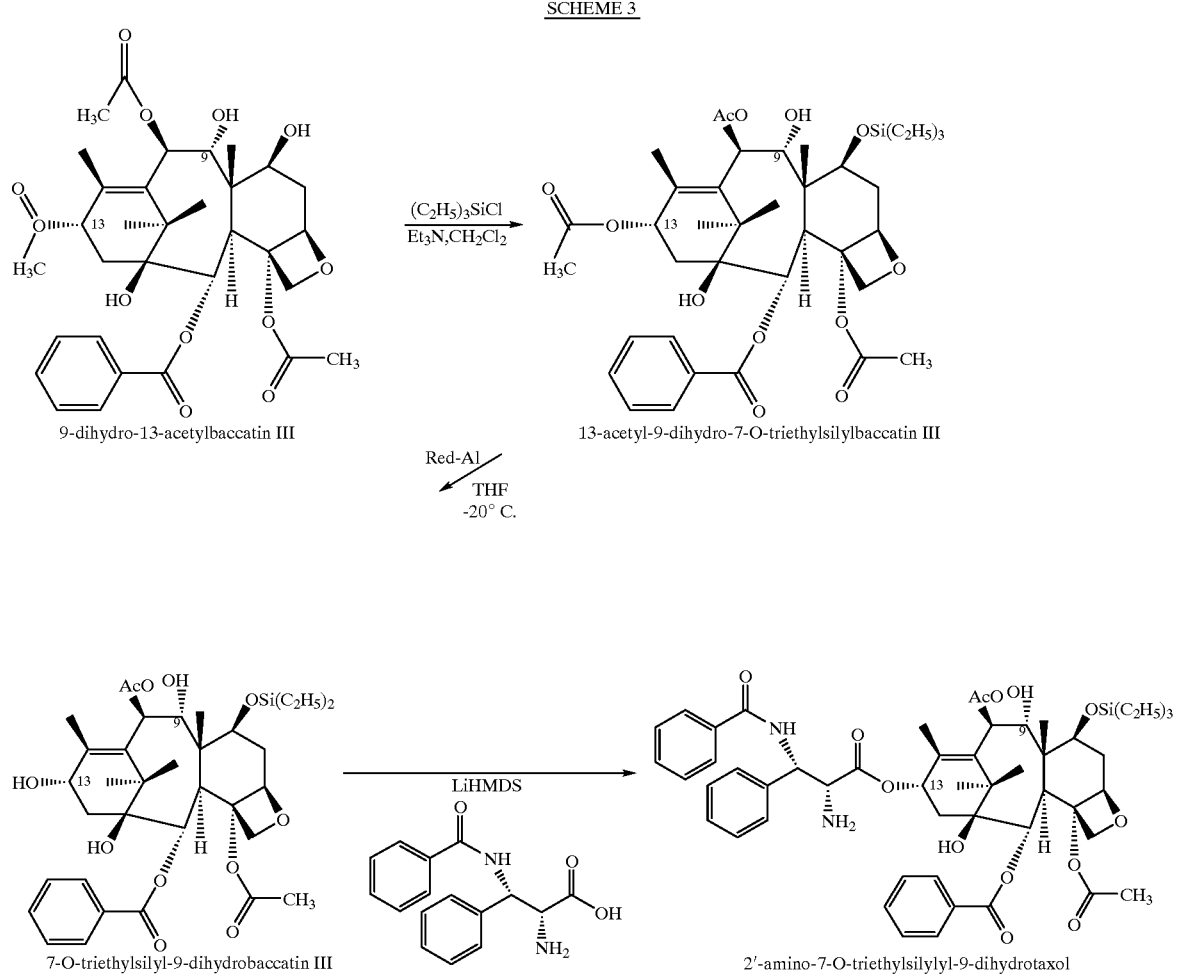

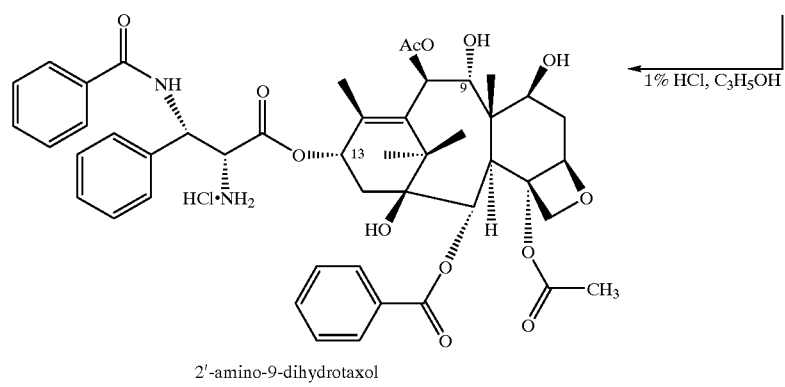
2'-amino-9-dihydrotaxol
SCHEME 4(a)
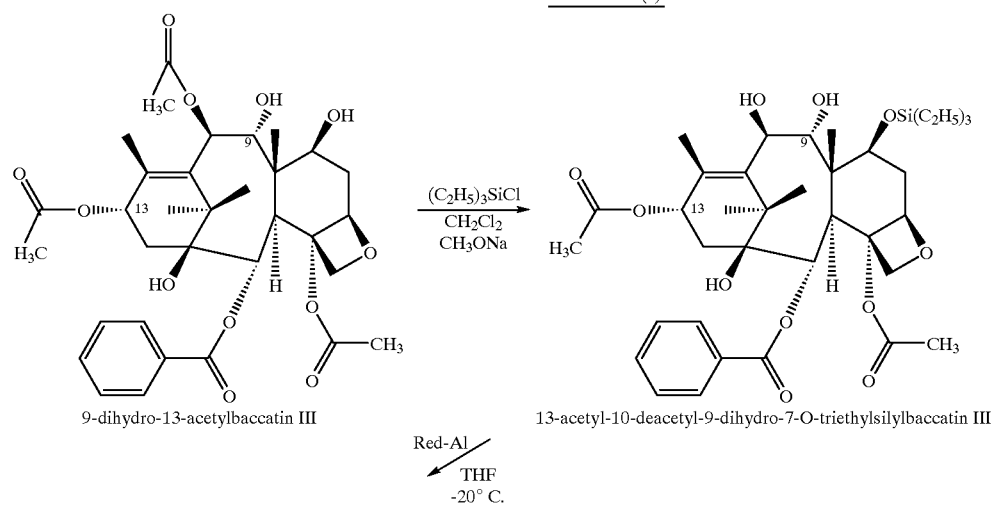
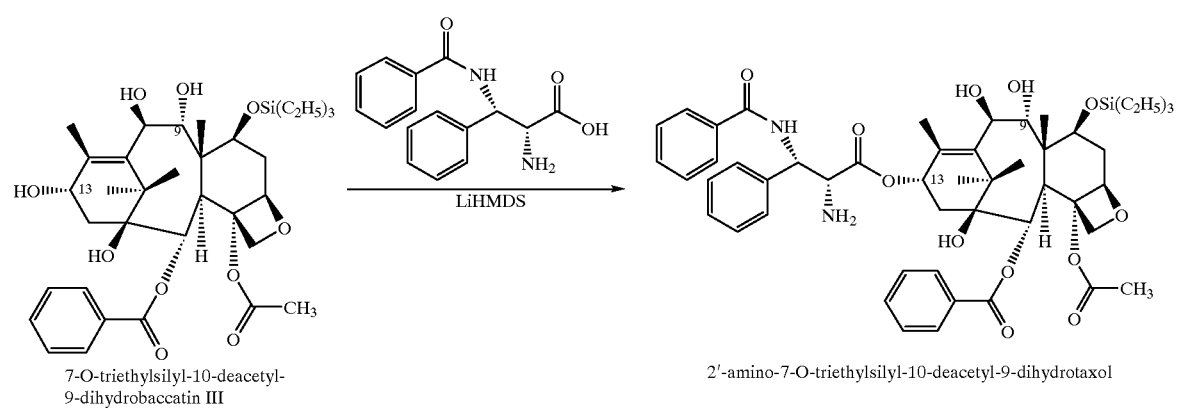

-continued

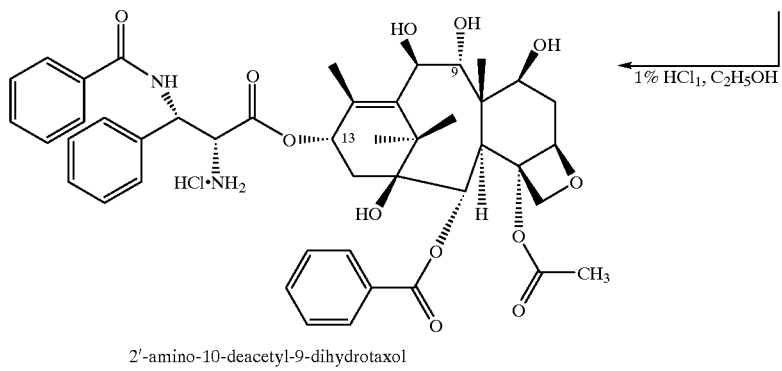

2′-amino-10-deacetyl-9-dihydrotaxol

SCHEME 4(b)

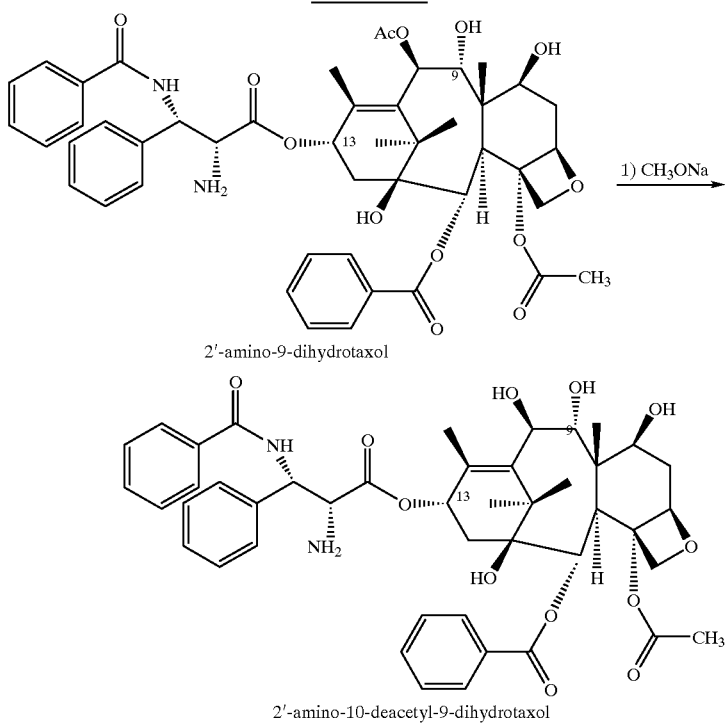

2′-amino-9-dihydrotaxol

2′-amino-10-deacetyl-9-dihydrotaxol

EXAMPLE 1

7-O-triethylsilyl-9-dihydro-13-acetylbaccatin III 1.0 g of 9-dihydro-13-acetylbaccatin III was placed into a 100 mL round bottom flask with 20 mL of dichloromethane ($CH_2Cl_2$). 5 mL of triethylamine ($Et_3N$), followed by 1.5 mole equivalent of triethylsilyl chloride (($C_2H_5$)$_3$SiCl) was added to the mixture, and the mixture was magnetically stirred for five hours at room temperature. The progress of the reaction was followed by thin layer chromatography (TLC). When TLC indicated that the reaction was completed, the mixture was poured into a 500 mL separator funnel containing 70 mL of water, and extracted with 100 mL dichloromethane. The organic phase was concentrated to dryness by vacuum, and the concentrate was purified by normal chromatography on silica gel, eluting with a mixture of dichloromethane and methanol (97.3) to yield 0.7 g of white crystal which was identified as 7-O-triethylsilyl-9-dihydro-13-acetylbaccatin Ill. The $^1$H-NMR data is as follows.

$^1$H-NMR (200 MHz, $CDCl_3$): 8.06 (d, Ar-H-2, H-6), 7.57 (t, A-H-4), 7.46 (dd, Ar-H-3, H-5), 6.15 (t, H-13), 6.14 (d, H-10), 5.73 (d, H-2), 5.34 (d, H-9), 4.92 (d, H-5), 4.55 (dd, H-7), 4.30 (d, H-20a), 4.14 (d. H-20b), 3.04 (d, H-3), 2.50 (m, H-6), 2.27 (s, $CH_3C=O$ ), 2.19 (s, $CH_3C=O$), 2.15 (H-14a), 2.11 (s, $CH_3C=O$), 2.00 (H-14b), 1.93 (s, $CH_3$), 1.80 (s, $CH_3$), 1.69 (s, $CH_3$), 1.24 (s, $CH_3$), 0.99 (t, 9H, 3$CH_3$), 0.74 (q, 6H, 3$CH_2$) ppm.

EXAMPLE 2

7-O-triethylsilyl-9-dihydrobaccatin III 100 mg of 7-O-triethylsilyl-9-dihydro-13-acetylbaccatin III from example 1 was placed in a 25 mL round bottom flask with 5 mL THF, at −44°' C., and five mole equivalent of methyl lithium ($CH_3Li$) were added dropwise to remove the acetyl group at the C-13 position of the 7-O-triethylsilyl-9-dihydro-13-acetylbaccatin III, and the reaction was monitored by TLC. When the deacetylation was completed, the mixture was partitioned between a mixture of saturated sodium hydrogencarbonate (NaHCO$_3$) or ammonium chloride (NH$_4$Cl) buffer and dichloromethane. The organic layer was concentrated to dryness, and the crude product was purified by flash column chromatography on silica gel, eluting with a mixture of dichloromethane and methanol (97:3) to yield 65 mg of 7-O-triethylsilyl-9-dihydrobaccatin III.

EXAMPLE 3

2'-amino-9-dihydrotaxol

Step 1

100 mg of 7-O-triethylsilyl-9-dihydrobaccatin III obtained from example 2 was placed in a 50 mL round bottom flask, with 10 mL of THF and 3 mole equivalent of lithium hexamethyldisilazide (LiHMDS) at −78° C. 3 mole equivalent of 2'-amino-3-benzoylamino-(2R, 3S)-3-phenyl-pyopionic acid was added and the mixture was warmed to −20° C. for five to ten hours. The mixture was quenched with 20 mL, of sodium hydrogencarbonate or ammonium chloride and 30 mL of dichloromethane. The organic layer was concentrated to dryness to give 2'-amino-7-O-triethylsilyl-9-dihydrotaxol.

Step 2

5 ml, of 1% hydrochloric acid was added to the 2'-amino-7-O-triethylsilyl-9-dihydrotaxol concentrate in 10 mL of ethanol solvent at 0° C. to remove the triethylsilyl (TES) protecting group. The resulting mixture was purified by flash column chromatography on silica gel, eluting with ethyl acetate:hexane (6:4) to yield 72 mg of white solid crystals which were identified as 2'-amino-9-dihydrotaxol.

EXAMPLE 4

13-acetyl-10-deacetyl-9-dihydro-7-O-triethylsilylbaccatin III 1.0 g of 9-dihydro-13-acetylbaccatin III was placed into a 100 mL round bottom flask with 20 mL of dichloromethane. 2 mole equivalent of sodium methoxide (NaOCH$_3$), followed by 1.5 mole equivalent of triethylsilyl chloride was added to the mixture, and the mixture was magnetically stirred for two to three hours at room temperature. The progress of the reaction followed by TLC. When TLC indicated that the reaction was completed, the mixture was poured into a 500 mL separator funnel containing 70 mL, of water, and extracted with 100 mL of dichloromethane. The organic phase was concentrated to dryness under vacuum. The concentrate was purified by flash column chromatography on silica gel, eluting with a mixture of ethyl acetate and hexane (55:45) to yield 750 mg of while crystals which were identified as 13-acetyl-10-deacetyl-9-dihydro-7-O-triethylsilylbaccatin III.

EXAMPLE 5

10-deacetyl-9-dihydro-7-O-triethylsilylbaccatin III 100 mg of 13-acetyl-10-deacetyl-9-dihydro-7-O-triethylsilylbaccatin III from example 4 was placed in a 25 mL round bottom flask with 10 mL of THF at −20° C. A 3 mole equivalent of Red-Al was added dropwise to remove the acetyl group at the C-13 position. The reaction program was monitored by TLC. When the deacetylation was complete the mixture was partitioned between a mixture of pH 7 phosphate and dichloromethane. The organic layer was concentrated to dryness, and the crude product was purified by flash column chromatography on silica gel, eluting with a mixture of dichloromethane and methanol (97:3) to yield 63 mg of 10-deacetyl-9-dihydro-7-O-triethylsilylbaccatin III.

EXAMPLE 6

2'-amino-10-deacetyl-9-dihydrotaxol

2'-amino-10-deacetyl-9-dihydrotaxol can be synthesized by the following two methods:

Method 1

Step 1

50 mg of 10-deacetyl-9-dihydro-7-O-triethylsilylbaccatin III obtained from example 5 was placed in 25 mL round bottom flask with 5 mL of THF and 3 mole equivalent of LiHMDS at −78° C. A 3 mole equivalent of 2'-amino-3-benzoylamino-(2R, 3S)-3-phenylpropionic acid was added and the mixture was warmed to −20° C. for five to ten hours. The mixture was quenched with 20 mL of pH 7 phosphate buffer, and extracted with 40 mL of dichloromethane. The organic layer was evaporated to dryness to give the intermediate 2'-amino- 10-deacetyl-7-O-triethylsilyl-9-dihydrotaxol.

Step 2

7 mL of 1% hydrochloric acid was added to 2'-amino-10-deacetyl-7-O-triethylsilyl-9-dihydrotaxol concentrate in the presence of 15 mL of ethanol at 0° C. to remove the TES protecting group. The mixture was purified by flash column chromatography on silica gel, eluting with ethyl acetate:hexane (6:4) to yield 35.5 mg of white solid crystals which were identified as 2'-amino-10-deacetyl-9-dihydrotaxol.

Method 2

100 mg of the product obtained for example 3, step 2 was placed in a 50 mL round bottom flask containing 20 mL of dichloromethane at 0° C. 3 mole equivalent of sodium methoxide was added and the mixture was magnetically stirred. The reaction was monitored by TLC. When TLC indicated that the reaction was completed, the mixture was partitioned between a mixture of water (30 mL) and dichloromethane (50 mL). The organic layer was concentrated to dryness, and the residue was purified to yield 50 mg of 2'-amino -10-deacetyl-9-dihydrotaxol.

EXAMPLE 7

7-O-tosyl-9-dihydro-13-acetylbaccatin III 1.0 g of 9-dihydro-13-acetylbaccatin III was placed in a 100 ml round bottom flask with 454 mg of p-toluene-sulfonyl chloride and 75 mg of tetrabutylammonium iodide. The mixture was dissolved in 25 ml of dichloromethane and stirred at room temperature for 10 minutes. Between 5 and 7 mg of sodium hydride was added slowly to the mixture, and then stirred at room temperature for 4 hours, following which 100 ml of water was added. The mixture was extracted with 70 ml of dichloromethane. The organic layer was concentrated to dryness, and the residue was purified by flash column chromatography on silica gel. Elution was achieved using a mixture of ethyl acetate and hexanes in a ratio of approximately 4:6, to yield 0.9 g of 7-O-tosyl-9-dihydro-13-acetylbaccatin III.

EXAMPLE 8

7-O-tosyl-9-dihydrobaccatin III 100 mg of the product obtained from example 7 was dissolved in 20 ml of tetrahydrofuran in a 50 ml round bottom flask. The flask was then placed into a container which was maintained at −44° C. The solution was stirred and 0.4 ml of methyllithium in hexane was added dropwise over a 5 minute period. The mixture was stirred for approximately 30 minutes with the temperature raised to approximately 0° C., and the mixture was partitioned between buffer and dichloromethane. The organic layer was evaporated to dryness. The residue was purified on a silica gel column using dichloromethane and methanol in a ratio of 97:3, to give 68 mg of 7-O-tosyl-9-dihydrobaccatin III.

EXAMPLE 9

2'-ethoxyethyl-7-O-tosyl-9-dihydrotaxol C 50 mg of 7-O-tosyl-9-dihydrobaccatin III was placed in a 25 ml round bottom flask and dissolved with 5 ml of tetrahydrofuran, and 6 mole equivalents of (2R, 3S)-N-hexanoyl-3-phenylisoserine, and 3 mole equivalents of lithium hexamethyidisilazide (LiHMDS) were added.

The mixture was stirred at −78° C. for approximately 20 minutes and then warmed to 0° C. over a 6 hour period or, until the reaction was completed as confirmed by TLC analysis. Once the reaction was completed, the mixture was quenched with 30 ml of a pH 7 buffer and the product was extracted with dichloromethane, dried and purified by preparative TLC on silica gel to yield 37 mg of 2'-ethoxyethyl-7-O-tosyl-9-dihydrotaxol C.

EXAMPLE 10

7-amino-9-dihydrotaxol C

Step 1

2'-ethoxyethyl-7-azide-9-dihydrotaxol C 30 mg of the product obtained from example 9, was dissolved in 5 ml of dry DMF, and into the solution was added 6 mg of sodium azide. The mixture was stirred at 60° C. for 5 hours. Once the reaction was completed, the mixture was partitioned between water and methylene chloride, dried with $MgSO_4$ and evaporated. The resulting residue was purified by preparative TLC to yield 18.5 mg of 2'-ethoxyethyl-7-azide-9-dihydrotaxol C.

Step 2

2'-ethoxyethyl-7-amino-9-dihydrotaxol C 50 mg of 2'-ethoxyethyl-7-azide-9-dihydrotaxol C was dissolved in methanol (10 ml), and 20 mg of Pd/C catalyst was added to the solution. The mixture was stirred in an atmosphere of hydrogen for 10 hours, or until the reaction was completed. The catalyst was filtrated and then the solvent was evaporated in a vacuum. The residue was crystallized from aqueous methanol to yield 2'-ethoxyethyl-7-amino-9-dihydrotaxol C as a white powder.

Step 3

7-amino-9-dihydrotaxol C

The product obtained from step 2, was dissolved in 5 ml of ethanol, and an excess of 1% hydrochloric acid was added. The mixture was maintained at room temperature for approximately 5 hours. The reaction was then quenched with 20 ml of water and partitioned between water and $CH_2Cl_2$. The organic layer was evaporated to dryness. The resulting residue was purified by preparative TLC. 7-amino-9-dihydrotaxol C was obtained as a white powder.

EXAMPLE 11

7-aminoethylamino-9-dihydrotaxol

Step 1

300 mg of 7-tosyl-9-dihydrobaccatin III and 850 mg of (2R, 3S)-N-benzoyl-0-(1-ethoxyethyl)-3-phenylisoserine was dissolved in THF (20 ml). 100 mg of NaH was added to the mixture at a temperature of between 0° C. and 5° C., and then stirred at room temperature for 5 hours until the reaction was completed, as monitored by TLC. The resulting mixture was then quenched with a pH 7 buffer and extracted with 50 ml of $CH_2Cl_2$, and the organic layer was washed with a saturated solution of $NaHCO_3$ and water. The $CH_2Cl_2$ solution was then concentrated to dryness under a vacuum, and the residue was purified by flash column chromatography to yield 2'-ethoxyethyl-7-tosyl-9-dihydrotaxol as a white powder.

Step 2

100 mg of the product of step 1, 2'-ethoxyethyl-7-tosyl-9-dihydrotaxol was placed in a 25 ml round bottom flask and dissolved in 10 ml of ethanol at room temperature. To the ethanol solution, 10 ml of ethylenediamine was added. The mixture was stirred at 60° C. for 5 hours, then cooled down to room temperature. An excess of 1% hydrochloric acid was added, and the mixture was stirred and maintained at room temperature for 3 hours. The reaction was then quenched with water and $CH_2Cl_2$. The organic layer was evaporated to dryness and purified by column chromatography to yield 73.5 mg of 7-aminoethylamino-9-dihydrotaxol.

I claim:

1. A compound having the formula:

wherein $R_4$ is a group having the formula:

in which $R_1$ and $R_2$ are independently selected from the group consisting of hydrogen, alkyl, aminoalkyl and alkanoyl;

$R_3$ is hydrogen or alkanoyl; and $R_5$ is selected from the group consisting of hydrogen, alkyl, phenyl, substituted phenyl, alkoxy, substituted alkoxy.

2. A compound having the formula:

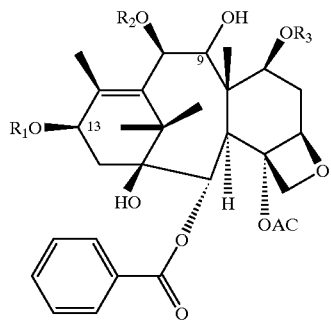

wherein $R_1$ is a group having the formula

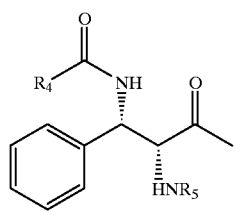

in which $R_2$ is hydrogen, alkanoyl or substituted alkanoyl;
$R_3$ is hydrogen or aminoalkanoyl;
$R_4$ is selected from the group consisting of phenyl, substituted phenyl, alkoxy, substituted alkoxy, alkyl, substituted alkyl; and
$R_5$ is selected from the group consisting of hydrogen, alkanoyl, aminoalkanoyl, and amino alkyl.

3. A compound having the formula:

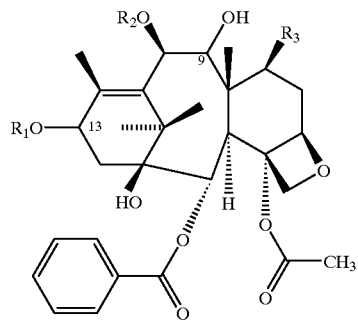

wherein $R_1$ is AC or H;
$R_2$ is H or alkanoyl; and
$R_3$ is selected from the group consisting of azide, amino, alkylamino, and polyamine.

4. A process for preparing 7-amine, alkylamino or polyamino-9-dihydro-paclitaxel derivatives, comprising the steps of:
a) protecting the C-7 hydroxyl group of 9-dihydro-13-acetylbaccatin III with a suitable phenyl-sulfonyl or substituted phenyl-sulfonyl protecting group; and
b) replacing the protecting group by an amine, oligoamine or polyamine functional group in a suitable reaction medium.

* * * * *